March 11, 1975 B. L. COBIA Plant Pat. 3,688

CACTACEAE PLANT

Filed Jan. 18, 1974

United States Patent

Plant Pat. 3,688
Patented Mar. 11, 1975

3,688

CACTACEAE PLANT

Barnell L. Cobia, Winter Garden, Fla., assignor to
B. L. Cobia, Inc., Winter Garden, Fla.

Filed Jan. 18, 1974, Ser. No. 434,450
Int. Cl. A01h 5/00
U.S. Cl. Plt.—88 1 Claim

ABSTRACT OF THE DISCLOSURE

A new and distinct hybrid plant variety of the Cactaceae family obtained through cross-pollination of plants of the *Zygocactus truncatus parma* variety and a *Zygocactus truncatus* variety known commercially as "Christmas Cheer" is principally distinguished from its parents and known related varieties by a growth habit which combines a fast growth rate, an upright and compact appearance with broader cladophylls than its maternal parent, substantially less flower bud abscission than its maternal parent, substantial resistance to nutrient deficiencies and fungus-type diseases, and a generally larger flower than its maternal parent and which has a bloom life from about 5 to about 8 days, perianth tube laminating tepals with marginal blade areas that in color are dominated by yellowish pink, pink red and/or purplish red hues, and perianth tube forming tepals with blades that are more recurve than those of the maternal parent and have marginal blade areas which in color are dominated by purplish red, red and/or pink hues.

The invention relates to a new and distinct plant variety of the Cactaceae family and which has been named the *Zygocactus truncatus* Kris Kringle by the inventor.

Certain plant varieties of the Cactaceae family are well known in the foliage plant market and among these are those of the *Zygocactus truncatus* variety commonly konwn as the "Christmas Cheer" variety. A lesser known variety that has appeared in the foliage plant market is the *Zygocactus truncatus parma*. These varieties tend to bolom in the months of November and December in the northern hemisphere and hence their appearance in the retail market area is primarily during the Thanksgiving and Christmas seasons.

The *parma* variety has what may be called a "reddish" colored bloom that is appealing to purchasers during the Thanksgiving-Christmas holiday season. The bloom life however varies from about 3 to about 6 days and this provides a tolerable shelf life to some merchants at the retail level of sales while others find the bloom life to be unacceptable. The variety suffers from the further disadvantage that many of the flower buds which start to mature fail to reach maturity and instead drop from the stems. Tests have indicated that this bud abscission problem is aggravated when the plant specimens are housed in closed cartons such as are used for shipping purposes in the industry. Growers are accordingly reluctant to grow the variety because of the transportation delays and large costs that are involved in manually selecting specimens for shipment which are at the proper stage of budding to provide reasonable assurance of mature blooming when the plants reach their destination. The variety also has a low tolerance to nutrient deficiencies and has a resistance to fungus-type diseases which is less than satisfactory to many growers.

The variety commonly known as "Christmas Cheer" has a bloom life which is generally acceptable to most retail merchants and which is in the area of from about 5 to 8 days. The bloom has what may be called a "salmon" color however and this color is less appealing to the general public during the Thanksgiving-Christmas season. There is accordingly a need for a *Zygocactus truncatus* variety which blooms in the Thanksgiving-Christmas season and has a "reddish" colored bloom and a bloom life which provides a suitable shelf life at the retail level of sales.

A general object of the invention has been to develop a variety of the Cactaceae family which would have a "reddish" colored bloom along with a more acceptable bloom life and resistance to flower bud abscisison than the *parma* variety. Yet another object of the invention has been to develop a variety having the foregoing general objective and which is faster growing and more compact in appearance than the *parma* variety.

The objectives of the invention have been fully realized by the development of the new plant variety hereinafter described in detail. The new plant variety was developed in a nursery located at Winter Garden, Fla., as a hybrid secured by cross-pollinating the flower of a plant of the *Zygocactus truncatus parma* variety with pollen from a plant of the *Zygocactus truncatus* variety commonly known as "Christmas Cheer." The seeds taken from the fertilized seed pod of the *parma* variety were cultivated at the mentioned nursery location and after prolonged observation of the seedlings the hybridized plant of the new plant variety was selected and asexually reproduced by the inventor at the Winter Garden nursery by the propagation of stem cuttings taken from the original hybrid Through successive propagations, it has been ascertained that plants of the new variety generally resemble the parent varieties but are distinguishable from the parent varieties and from other related varieties known to the inventor by a growth habit which is evident in plants propagated and grown under nursery conditions utilized in the growing of tropical plants at Winter Garden, Fla., as combining the following principal characterisitcs:

1. A faster growth rate than its maternal parent,
2. A more upright and compact (denser) appearance than its parents, as evidenced by more erect stems with heavier (more frequent) branching,
3. Broader cladophylls than its maternal parent,
4. Substantially greater resistance to flower bud abscission than its maternal parent,
5. Greater resistance to nutrient deficiencies and fungus-type diseases than its parents, and
6. A generally larger flower than its maternal parent and which has (a) A bloom life from about 5 to about 8 days,
(b) Perianth tube laminating tepals with marginal blade areas that in color are dominated by yellowish pink, pink, red and/or purplish red hues, and
(c) Perianth tube forming tepals with blades that are more recurved than those of the maternal parent and marginal blade areas that in color are dominated by purplish red, and/or pink hues.

The accompanying drawing serves, by color photographic means, to illustrate the new plant variety and wherein.

Figure 1:
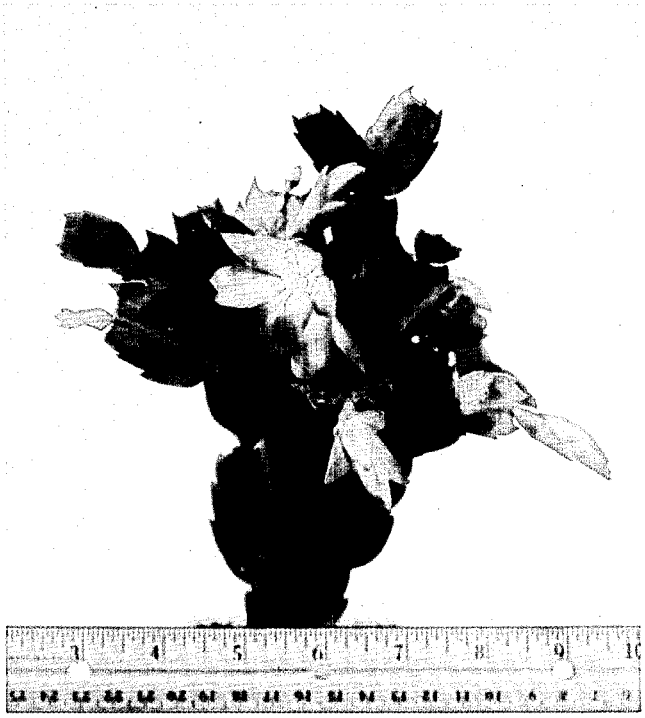
FIG. 1 is a color photograph of a plant specimen of the new plant variety.
Figure 2:
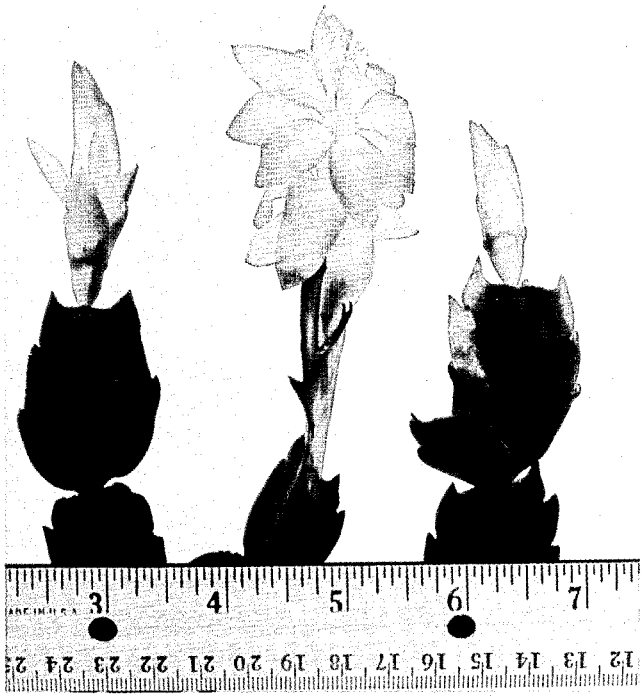
FIG. 2 is a color photograph showing a fully opened bloom of the new variety together with buds of the new variety in earlier stages of bloom maturity.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than one year of age from initial propagation and which were grown under 50–70% shaded glasshouse nursery conditions in the Winter Garden, Fla., area and wherein temperatures range from 60 to 85° F. during the winter months, from 75 to 95° F. during the summer months and are ambient during intervening periods.

DETAILED PLANT DESCRIPTION

Name: *Zygocactus truncatus Kris Kringle.*

Parentage:

*A. Maternal.*—*Zygocactus truncatus parma.*

*B. Paternal.*—*Zygocactus truncatus* variety known commercially as "Christmas Cheer."

Classification:

*A. Botanic (Britton and Rose, The Cactaceae, Constable and Co., Ltd., London, 1937, Vol. IV).*—(1) Family: Cactaceae. (2) Tribe: Cereeae. (3) Sub-tribe: Epiphyllanae. (4) Genus: Zygocactus. (5) Species: *truncatus* (Haworth) Schuman.

*B. Commercial.*—Thanksgiving-Christmas blooming cactus.

Form: Terrestrial, shade-loving, succulent, leafless plant with jointed and branched stems.

Stems:

*A. General.*—Irregular with usually multi-chotomous branching of both upright and pendulous, adventitiously rootable, flattened cladophylls that have a prominent midrib and prominently toothed lateral wings.

*B. Cladophylls.*—(1) General: Elongated and flat with transversely elongated, areole bearing, truncated apex, with inwardly tapering basal wing margins that merge through a broad usually pointed basal juncture with the cladophyll therebelow, and with an axially areole associated with each tooth. (2) Midrib (a) General—Extends longitudinally of cladophyll and continuously through joints with laterally tapering cortex at wing insertions. Pith surrounding vascular bundles that branch and provide lateral extensions of the vascular system to marginal teeth. (b) Texture—Smooth waxy epidermis with wax in small embedded scales and becoming corky in basal stem areas with age. (c) Size (2–6 mos. old)—(1) Length—Usually between 25 and 50 mm. (2) Thickness—Usually between 2.0 and 5.5 mm. with the average for respective plant specimens being usually between 3.0 and 4.0 mm. (d) Color (at maturity)—Commonly moderate olive green (5 GY 4/4) (7.5 GY 4/4) (7.5 GY 4/6). (3) Wings: (a) General shape—Generally flattened from midrib cortex to tooth insertions with slight thinning taper toward margins. (b) Margins — Toothed (modified leaves). (c) Texture—Succulent to leathery with smooth waxy epidermis having wax arranged in small embedded scales and becoming corky in basal plant areas with age. (d) Size (2–6 mos. old)—(1) Center thickness—Usually between 0.75 and 2.0 mm. (2) Width (as measured from cladophyll axis to most offset lateral areole—Usually between 10 and 16 mm. (e) Color (at maturity)—Commonly moderate olive green (5 GY 4/4) (7.5 GY 4/4) (7.5 GY 4/6). (4) Teeth: (a) General shape—Generally flattened and tapered along margins from wing insertions to an apex having a hyaline, single cell, pointed spine with nonpredictable bending, with a generally straight adaxial margin having some tendency toward concave curvature, and with abaxial margins that usually vary from convex for the proximal and distally located teeth to generally straight at intervening locations. (b) Orientation—Usually projects generally distally of cladophyll base in an alternate arrangement and with the median of the tooth angles (as measured at the distal side of the intersect with the cladophyll axis of a line through the tooth apex and the midpoint between the abaxial and adaxial areoles thereof) formed by the non-basal teeth of a cladophyll usually being between 1° and 17°. (c) Margins—Entire. (d) Texture—Succulent to leathery with smooth waxy epidermis having wax in small embedded scales and becoming corky in basal plant areas with age. (e) Number—Usually from 6 to 7 and commonly 8 per cladophyll. (f) Size (2–6 mos. old)—(1) Center thickness—usually between 0.4 and 0.9 mm. (2) Areole to apex dimension (adaxial marginal side)—Usually between 1 and 5 mm. (g) Color (at maturity)—Commonly moderate olive green (5 GY 4/4) (7.5 GY 4/4) (7.5 GY 4/6). (5) Areoles: (a) Terminal areole—Large elongated oval-shaped with several acicular bristles, copious multicellular hairs, and several buds that may mature into either new cladophylls or flowers. The opposite ends of the areole are located adjacent to subsidiary areoles which are in turn located at the axils of teeth that are located at the distal end of cladophyll. (b) Axillary aeroles—Acicular bristles without glochidia but having copious, short, brownish to colorless, multicellular hairs. In areoles that are located below the teeth at the distal end of the cladophyll, there is usually only one bud that is frequently latent.

Buds: Unarmored, ovoid and chlorophyllous.

Flowers:

*A. General.*—Sessile, zygomorphic, usually solitary, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

*B. Sepaloid series.*—(1) General: Free tepals inserted on top of ovary. (2) Shape: Tapered from insertion to apex in outer members of whorl and grading inwardly in the whorl to provide progressively broader apices and longer base-tip dimensions. All members have pointed tip and entire margins with sparse irregular teeth appearing mainly in apex areas of the inner members of the whorl. (3) Texture: Succulet and glabrous outer whorl members and grading inwardly in the whorl to silken blades with fleshy basal areas. (4) Number: Usually from 8 to 10. (5) Size (at full bloom): (a) Base-tip dimension—Usually less than 35 mm. (b) Maximum width dimension—Usually less than 15 mm. (6) Color: Outer whorl tepal members have marginal areas which in color are dominated by reddish orange, pink and/or red hues and basal areas which in color are dominated by a yellow green hue with the colors in the marginal and basal areas tending to surround and merge inwardly with a translucent white center field. Commonly strong yellow green (5 GY 7/8) (5 GY 6/8), moderate yellow green (5 GY 7/6) (2.5 GY 7/6) (5 GY 6/6) and/or light yellow green (2.5 GY 8/6) in basal areas and vivid red (5 R 4/14), strong red (5 R 5/12), moderate red (2.5 R 5/10), deep pink (2.5 R 6/10), strong reddish orange (7.5 R 5/12) and/or moderate reddish orange (7.5 R 5/10) (7.5 R 6/8) in marginal areas. Inner whorl tepal members have translucent white basal areas that extend distally in the tepal and merge with marginal blade areas which in color are dominated by purplish pink, purplish red, red and/or reddish orange hues. Commonly purplish pink (7.5 RP 6/10), moderate purplish red (7.5 RP 5/10) (10 RP 5/10) (10 RP 4/10), deep pink (10 RP 6/10) (2.5 R 6/10) (5 R 6/10), moderate red (2.5 R 5/10) (2.5 R 4/10), strong red (5 R 5/12) (5 R 4/12), vivid red (5 R 4/14), deep reddish orange (near 7.5 R 4/2) and/or strong reddish orange (7.5 R 5/12) in marginal areas. (7) Orientation at full bloom: Varying inwardly in the whorl from erect to recurve.

C. *Tube laminating series.*—(1) General: Tepals inserted on ovary and basally united below the throat as outer laminations on the perianth tube and with progressively greater amounts of basal fusion inwardly in the whorl. (2) Shape: Grading inwardly in whorl with progressively longer base-tip dimensions and progressively broader apices so that blade area changes inwardly from ovate with acuminate tendencies to spactulate with acute tips. Entire margins with sparse irregular teeth mainly in apex areas. (3) Texture: Succulent, slightly fleshy, basal areas with silken blades. (4) Number: Usually 4 or 5. (5) Size (at full bloom): (a) Base-tip dimensions—Usually between 30 and 50 mm. (b) Maximum width dimensions—Usually between 13 and 16 mm. (6) Color: Tepals with translucent white basal areas that extend distally in the tepal and merge with marginal blade areas that in color are dominated by yellowish pink, pink, red and/or purplish red hues. Commonly strong yellowish pink (near 5 R 7/8), deep pink (10 RP 6/10) (2.5 R 6/10) (5 R 6/10), vivid red (5 R 4/14), strong red (near 5 R 5/12), moderate red (2.5 R 5/10) and/or moderate purplish red (10 RP 5/10) in marginal blade areas. (7) Orientation at full bloom: Recurved.

D. *Tube forming series.*—(1) General: Tepals basally united to form hollow perianth tube that is inserted on ovary and equipped with irregular carina (keel) at throat. (2) Shape: (a) Perianth tube—Elongated and ellipsoidal in cross section with major ellipsoidal axis commonly arranged generally parallel to or at an acute angle with respect to the general plane of the supporting cladophyll. (b) Blades—Nearly zygomorphic, thin spatulate with acute tip. Entire margins with sparse, irregular teeth mainly in apex area. (c) Carina (keel)—Irregular and transcending. (3) Texture: (a) Perianth tube—Thick, succulent and slightly ribbed. (b) Blades—Translucent and silken. (c) Carina (keel)—Fleshy. (4) Blade number: Usually 8 or 9. (5) Size (at full bloom): (a) Perianth tube—(1) Base to keel length—Usually between 30 and 40 mm. (2) Internal major axis (at throat)—Usually between 8 and 11 mm. when measured perpendicular to axis of perianth tube. (3) Internal minor axis (at throat)—Usually between 6 and 9 mm. when measured perpendicular to axis of perianth tube. (b) Blades—(1) Length (keel to tip)—Usually between 25 and 35 mm. (2) Width (maximum)—Usually between 10 and 17 mm. (6) Color (at full bloom): (a) Perianth tube—A translucent white. (b) Blades—Tepal blades with marginal blade areas which in color are dominated by purplish red, red and/or pink hues that merge with a translucent white basal blade area located distally of the keel. Commonly moderate purplish red (10 RP 5/10), moderate red (2.5 R 5/10) (2.5 R 4/10), deep pink (2.5 R 6/10 (10 RP 6/10), strong pink (2.5 R 7/8), moderate pink (5 R 7/6) (2.5 R 7/6) and/or light-moderate pink (10 RP 8/4) (2.5 R 8/4) in marginal areas. (c) Carina (keel)—Commonly strong reddish purple (10 P 5/10) (2.5 RP 5/10), dark purplish pink (5 RP 6/8), light reddish purple (2.5 RP 6/8) and/or deep purplish pink (5 RP 6/10). (7) Orientation at full bloom: Erect to recurve.

E. *Androecium (stamens).*—(1) General: Numerous exserted and diadelphous stamens with one group having filaments basally fused to the perianth tube and the other group having filaments basally united to form a nectary housing, thin annulus around the style and which is provided with a thin, deflexed, irregular toothed margin or ruffle at the throat of the annulus. (2) Stamen number: (a) Tube attached group—Usually between 78 and 85. (b) Basally united group—Usually between 18 and 22. (3) Filament: (a) General—Translucent and glabrous with anther connective. (b) Shape—Long, slender and gradually tapering from base to anther connective. (c) Texture—Glabrous and silken. (d) Color—A translucent white. (e) Size (at full bloom)—(1) Length—(a) Tube attached group—Usually between 35 and 52 mm. (b) Basally united group—Usually between 42 and 51 mm. (2) Diameter—Usually between 0.2 and 0.3 mm. intermediate the opposite ends. (4) Anthers: (a) General—Adnate with four longitudinally dehiscent pollen sacs. (b) Shape—Elongated. (c) Texture—Waxy. (d) Color (prior to dehiscing)—Usually pale yellow (5 Y 9/4) and/or pale yellowish green (7.5 Y 9/4). (e) Size (immediately prior to dehiscing)—Usually between 0.8 and 2.1 mm. in length. (f) Sterility—Very fertile.

F. *Gynoecium (pistil).*—(1) General: Compound, parietal placentation with united style surrounded by annular diffuse nectary at its insertion. (2) Style: (a) General—Hollow, stout and inserted in ovary. (b) Shape—Elongated, cylindrical and generally tapering. (c) Texture—Fleshy and glabrous with short inner glutinous hairs as distal end. (d) Color—Commonly deep purplish pink (5 RP 6/10), (7.5 RP 6/10), deep pink (10 RP 6/10), moderate purplish red (near 10 RP 5/10) and/or moderate red (2.5 R 5/10) at distal end. (e) Size (at full bloom)—(1) Length—Usually between 54 and 63 mm. (2) Diameter—Usually between 0.6 and 0.9 mm. intermediate the opposite ends. (3) Stigma: (a) General—Exserted and erect with usually 6 inner marginally adhering lobes that exhibit a general tendency for bifurcation. (b) Shape—Elongated and tapering toward lobe tips and having relatively blunt apices. (c) Texture—Fleshy and smooth with short glutinous hairs. (d) Color—Commonly deep purplish pink (5 RP 6/10) (7.5 RP 6/10), deep pink (near 10 RP 6/10), moderate purplish red (near 10 RP 5/10) and/or moderate red (2.5 R 5/10). (e) Size (lobe length at full bloom)—Usually between 4.5 and 5.0 mm. along inner margins. (4) Ovary: (a) General—Epigynous with thin epidermis and distally located concavity and with single cavity having 6 carpels with numerous ovules. (b) Shape—Terete to ovoid and generally broadening from insertion to floral end. (c) Texture—Succulent and glabrous with thin outer epidermis. (d) Color—Commonly strong yellow green (5 GY 7/8) (5 GY 6/8), moderate yellow green (5 GY 7/6) (2.5 GY 7/6) (5 GY 6/6), and/or light yellow green (2.5 GY 8/6). (e) Size (at full bloom)—(1) Length (insertion to concavity base)—Usually between 6 and 11 mm. (2) Major axis (distal end of concavity)—Usually between 6 and 10 mm. (3) Minor axis distal end of concavity)—Usually between 6 and 9 mm. (f) Sterility factor—Very fertile.

Growing characteristics: A fast growth rate with the production of more than 1.5 times the number of mature cladophylls during comparable growing periods than either parent, a more upright and compact (denser) appearance than its parents, as evidenced by more erect stems with heavier (more frequent) branching, a greater resistance than its parents to nutrient deficiencies and to fungus-type diseases, a bloom life (from initial tepal separation to initial tepal withering) of from about 5 to about 8 days and substantially less flower bud abscission than its maternal parent.

The following is a general description of a specimen of the new plant variety that was grown from the propagation of a single cladophyll in a nursery at Winter Garden, Fla.

Age or plant: 12 months from initial propagation.
Branches from propagated cutting: 4.
Total number of cladophylls grown from cutting: 66.

General:

| Branch No. | No. of cladophylls | Max. length, mm. | No. of tips |
|---|---|---|---|
| 1 | 9 | 119 | 5 |
| 2 | 14 | 203 | 8 |
| 3 | 6 | 146 | 2 |
| 4 | 37 | 252 | 15 |

Midribs:

| Branch No. | Length (avg.), mm. | Thickness (avg.), mm. |
|---|---|---|
| 1 | 41 | 2.87 |
| 2 | 46 | 3.62 |
| 3 | 38 | 3.50 |
| 4 | 40 | 3.73 |

Wings:

| Branch No. | Center thickness (avg.), mm. | Max. width (avg.), mm. |
|---|---|---|
| 1 | 1.45 | 11.7 |
| 2 | 1.62 | 14.1 |
| 3 | 1.50 | 13.2 |
| 4 | 1.73 | 14.3 |

Teeth:

| Branch No. | No. cladophylls (avg.) | Center thickness (avg.), mm. | Areole to apex dimension (avg.), mm. | Tooth angle (median), ° |
|---|---|---|---|---|
| 1 | 6 | 0.65 | 2.7 | 3 |
| 2 | 6 | 0.75 | 1.3 | 6 |
| 3 | 6 | 0.66 | 2.5 | 12 |
| 4 | 6 | 0.76 | 4.3 | 9 |

Cladophyll color: Moderate olive green (7.5 GY 4/6).

The following is a general description of a flower of the new plant variety which bloomed in November on a plant grown under shaded glasshouse nursery conditions in Winter Garden, Fla.

Bloom life: 8 days.
Sepaloid series of tepals:
(1) *Number.*—9.
(2) *Size at full bloom).*—(a) Maximum base-tip dimension—26 mm. (b) Minimum base-tip dimension—4 mm. (c) Maximum width dimension—14 mm.

(3) *Color.*—Moderate yellow green (5 GY 7/6) (5 GY 6/6) in basal areas and strong red (5 R 5/12), moderate red 2.5 R 5/10) and deep pink (2.5 R 6/10) in marginal areas of outer whorl members. Moderate red (2.5 R 5/10), strong red (5 R 5/12) and deep reddish orange (near 7.5 R 4/12) in marginal areas and a translucent white in basal areas of inner whorl members.

Tube laminating series:
(1) *Number.*—7.
(2) *Size (at full bloom).*—(a) Maximum base-tip dimension—45 mm. (b) Minimum base-tip dimension—31 mm. (c) Maximum width dimension—18 mm. (d) Minimum width dimension—13 mm.
(3) *Color.*—Deep pink (10 RP 6/10) (5 R 6/10), vivid red (5 R 4/14), strong red (near 5 R 5/12) and moderate red (2.5 R 5/10) in blade areas and translucent white in basal areas.

Tube forming series of tepals:
(1) *Number.*—8.
(2) *Size (at full bloom).*—(a) Perianth tube—(1) Base to keel length—37 mm. (2) Interior major axis (at throat)—10 mm. (3) Interior minor axis (at throat)—8 mm. (b) Blades—(1) Maximum length (keel to tip)—28 mm. (2) Minimum length (keel to tip)—26 mm. (3) Maximum width—16 mm. (4) Minimum width—13 mm.
(3) *Color.*—(a) Perianth tube—A translucent white. (b) Blades—Deep pink (2.5 R 6/10), strong pink (2.5 R 7/8), moderate pink (5 R 7/6) and moderate red (2.5 R 5/10) in blade areas with translucent white area adjacent keel on upper epidermis and a translucent white basal area on lower epidermis. (c) Carina (keel)—Dark purplish pink (5 RP 6/8), light reddish purple (2.5 RP 6/8) and deep purplish pink (5 RP 6/10).

Androecium:
(1) *Stamen number.*—(a) Tube attached group—82. (b) Basally united group—19.
(2) *Filaments.*—(a) Color—A translucent white. (b) Size (at full bloom)—(1) Length—(a) Tube attached group—46 mm. (avg.). (b) Basally united group—47 mm. (avg.) (2) Diameter—About 0.25 mm. intermediate the opposite ends.
(3) *Anthers.*—(a) Color (before dehiscing)—Pale yellowish green (7.5 Y 9/4). (b) Size—1.7 mm. (avg.). (c) Sterility—Very fertile.

Gynoecium (pistil):
(1) *Style.*—(a) Color—Moderate purplish red (near 10 RP 5/10). (b) Size (at full bloom)—(1) Length—61 mm. (2) Diameter—About 0.7 mm. intermediate the opposite ends.
(2) *Stigma.*—(a) Color—Deep purplish pink (7.5 RP 6/10). (b) Size (lobe length)—About 5 mm.
(3) *Ovary.*—(a) Color—Moderate yellow green (5 GY 7/6). (b) Size (at full bloom)—(1) Length insertion to concavity base)—9 mm. (2) Major axis (distal end of concavity—8 mm. (3) Minor axis (distal end of concavity)—7 mm. (c) Sterility—Very fertile.

I claim:

1. The new and distinct hydrib plant variety of the Cactaceae family as described and illustrated and which is principally distinguished by a growth habit that combines the following characteristics:
(1) A faster growth rate than its maternal parent,
(2) A more upright and compact appearance than its parents,
(3) Broader cladophylls than its maternal parent,
(4) Substantially less flower bud abscission than its maternal parent,
(5) Greater resistance to nutrient deficiencies and fungus-type diseases than its parents, and
(6) A generally larger flower than its maternal parent and which has (a) a bloom life from about 5 to about 8 days,
(b) perianth tube laminating tepals with marginal blade areas that in color are dominated by yellowish pink, pink, red and/or purplish red hues, and
(c) perianth tube forming tepals with blades that are more recurved than those of the maternal parent and have marginal blade areas which in color are dominated by purplish red, red and/or pink hues.

References Cited

UNITED STATES PATENTS

P.P. 3,574 6/1974 Cobia ---------- Plants—88

ROBERT E. BAGWILL, Primary Examiner

PO-1050
(5/69)

UNITED STATES PATENT OFFICE
CERTIFICATE OF CORRECTION

Patent No. PP. 3,688 Dated March 11, 1974

Inventor(s) Barnell L. Cohia

It is certified that error appears in the above-identified patent and that said Letters Patent are hereby corrected as shown below:

Column 1, Line 41, "bolom" should read -- bloom --;
Column 2, Line 33, after "hybrid" insert -- plant --;
Line 60, before "and/or" insert -- red --;
Column 3, Line 51, "axially" should read -- axillary --;

Signed and Sealed this

Twenty-seventh Day of July 1976

[SEAL]

*Attest:*

RUTH C. MASON
*Attesting Officer*

C. MARSHALL DANN
*Commissioner of Patents and Trademarks*